United States Patent [19]

Stepaniuk et al.

[11] Patent Number: 4,822,927
[45] Date of Patent: Apr. 18, 1989

[54] CONTINUOUS DECOMPOSITION OF DIAZONIUM FLUORIDES

[75] Inventors: Nickolas J. Stepaniuk, Chesterfield; Bruce J. Lamb, St. Charles, both of Mo.

[73] Assignee: Mallinckrodt, Inc., St. Louis, Mo.

[21] Appl. No.: 124,501

[22] Filed: Nov. 24, 1987

[51] Int. Cl.$^4$ .................. C07C 17/22; C07C 25/13; C07C 41/22; C07D 211/72
[52] U.S. Cl. .................. 570/141; 546/180; 546/312; 546/345; 568/656
[58] Field of Search .............. 570/141; 568/656; 546/180, 312, 345

[56] References Cited

U.S. PATENT DOCUMENTS 2,606,183  8/1952  Head et al. ..................... 568/656
3,160,623  12/1964  Annello et al. ................ 570/141
3,423,391  1/1969  Kindler et al. ................. 260/141
3,703,521  11/1972  Boudakian ..................... 546/345
4,096,196  6/1978  Boudakian ..................... 546/345

FOREIGN PATENT DOCUMENTS 205019  12/1986  European Pat. Off. ........... 17/22
3520316  12/1986  Fed. Rep. of Germany ...... 570/141
49-81330  8/1974  Japan .

Primary Examiner—J. E. Evans
Attorney, Agent, or Firm—Bernard, Rothwell & Brown

[57] ABSTRACT

Disclosed is a process for continuous preparation of aromatic fluorides wherein aromatic diazonium fluorides are continuously decomposed at low concentration in a reaction system of one or more continuous agitated reactors.

12 Claims, 1 Drawing Sheet

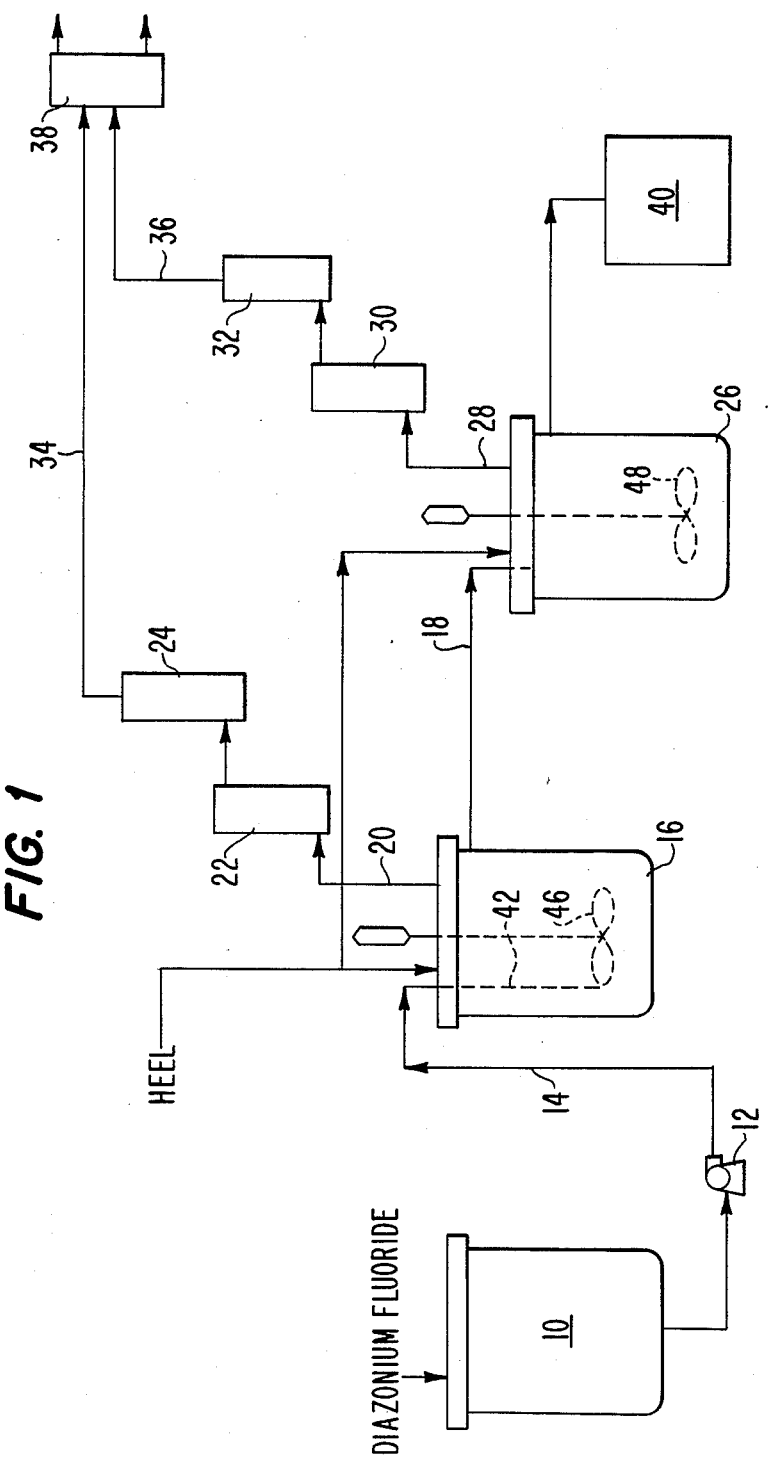

CONTINUOUS DECOMPOSITION OF DIAZONIUM FLUORIDES

BACKGROUND OF THE INVENTION

This invention relates to a process for continuous preparation of aromatic fluorides wherein corresponding aromatic diazonium fluorides are continuously decomposed at low concentration in a reaction system including one or more continuous flow through cascaded reactors.

Aromatic fluorides prepared in accordance with the present invention are useful as intermediates in preparing various pesticides, pharmaceuticals and other products.

Processes have heretofore been proposed for preparation and further reaction of aromatic diazonium salts as well as preparation of fluoroaromatics involving decomposition of corresponding diazonium fluorides.

Kindler, U.S. Pat. No. 3,423,391, discloses a process for the continuous diazotization, particularly at relatively high temperatures, of amines with diazotizing agents and for the further reaction of the resultant diazo compounds or allegedly for their recovery as such. According to the patent, further processing of the diazo compounds thus formed into azo dyes, phenols, hydrazines or other compounds capable of being prepared therefrom may also be carried out, preferably continuously, in reactors of conventional types, for example in flow tubes, agitated vessels or a cascade of such vessels or a circulation reactor. The patent discloses that the diazo compounds obtained are separated or further reacted so rapidly that no appreciable amounts of decomposition products can form. According to the patent, substantially all (e.g., at least 50%) of the heat of reaction from the continual mixing and reacting of the amine and the diazotizing agent is absorbed by the reaction mixture, the temperature thereof rising by from 20° C. to 50° C. or more, and the diazo compounds formed are obtained at 40° C. to 80° C. or, in case of high melting point or sparingly soluble components, to 100° C. or even higher.

Japanese Patent Publication No. 49[1974]-81330, published Aug. 6, 1974, discloses a method for preparation of aromatic fluoro componds wherein a hydrofluoric acid solution of a compound that gives nitrous acid is allowed to act on a substituted or unsubstituted aromatic amino compound and diazotization and thermal decomposition of the diazonium salts produced are carried out in one step at a reaction temperature that causes thermal decomposition of the diazonium salts. According to the disclosure, the method has the advantage that either the batch method or continuous method can be used, and usually the reaction is carried out by continuously introducing a hydrofluoric acid solution of the compound that provides nitrous acid into a hydrofluoric acid salt or solution of the aromatic amino compound.

European Patent Application No. 205,019, to Riedel DeHaen AG, discloses a process for producing aromatic fluorides wherein aromatic diazonium fluoride is first prepared and then the aromatic diazonium fluoride is decomposed in a falling-film reactor. Typically, falling film reactors are vertical tubular reactors in which the reactor walls are heated to raise the temperature of the reactants. A rotating device in the center of the tube spreads the reactants in a thin film on the reactor walls. In the decomposition of aromatic diazonium fluoride, HF flashes off as the reactants move down the reactor walls. Unfortunately, it is difficult or impossible to control the temperature of the reactants. Consequently, in the decomposition of aromatic diazonium fluorides, the temperature of the reactants is allowed to seek its highest point, with the result that undesirable by products can form. Furthermore, the falling film reactor is mechanically complex and subject to by-product fouling. Another potential problem with the falling film reactor is that unreacted diazonium fluoride can build up in the reactor outlet. Large concentration build up of diazonium fluoride presents a safety hazard inasmuch as the diazonium fluoride can release a substantial amount of energy upon decomposition.

The heretofore known processes for preparing fluoroaromatic compounds via decomposition of corresponding aromatic diazonium fluorides have not been entirely satisfactory in that they typically are complex, inefficient, expensive, non-continuous and/or prone to result in an unacceptably high level of tar and/or other byproducts. Accordingly, there is a substantial need in the art for a continuous diazonium fluoride decomposition process which would overcome these disadvantages. There is also a need for a process for decomposing aromatic diazonium fluorides which provides for the facile control of temperature and concentration of the aromatic diazonium fluoride in order to optimize yield, minimize undesired by products and avoid unnecessary safety hazards.

DESCRIPTION OF THE INVENTION

Generally stated, the present invention provides a process for continuous preparation of an aromatic carbocyclic or heterocyclic fluoride from the corresponding aromatic diazonium fluoride, which comprises:

(a) continuously introducing to one or more reaction vessels a liquid feed solution of an aromatic diazonium fluoride in hydrogen fluoride;

(b) continuously agitating the reaction mixtures in the reaction vessels while heating the contents of the vessels to a temperature sufficient to decompose said diazonium fluoride; and (c) continuously withdrawing reaction mixture from each of said reaction vessels and feeding withdrawn reaction mixture to the next successive vessel until the decomposition of said diazonium fluoride is substantially complete, the withdrawal and feed rates being sufficient to maintain the concentration of diazonium fluoride in the reaction mixtures in each of the vessels at not more than 2.0 gram-moles per liter, perferable not more than 0.5 gram-moles per liter.

In a preferred embodiment of the invention, two sequential reaction vessels are employed.

The maintenance of low diazonium fluoride concentration in the vessels, i.e. below 2.0 gram-moles/liter, is essential to the obtainment of high yields of the desired aromatic fluoride. It is believed that the decomposition of diazonium salt forms a reaction intermediate that is attacked by any nucleophile present. Dilution with HF reduces by product formation. The literature teaches this intermediate is probably a phenyl cation. By maintaining a low concentration of diazonium fluoride, yield losses and the associated formation of troublesome by products are substantially avoided. By products have been observed to form a separate phase which leads to emulsions and phase separation problems.

BRIEF DESCRIPTION OF THE DRAWING

FIG. 1 is a schematic illustration of the process of the invention in which an aromatic diazonium fluoride is decomposed to produce the corresponding aromatic fluoride in a two-stage continuous stirred reactor system.

DETAILED DESCRIPTION OF THE INVENTION AND OF THE MANNER AND PROCESS OF MAKING AND USING IT

Aromatic diazonium fluorides for decomposition to aromatic fluorides in accordance with the decomposition-fluorination process of this invention may be prepared by any suitable method. A number of heretofore known methods for converting aromatic primary amines to their corresponding aromatic diazonium fluorides are suitable. Such methods are based on the chemical reaction represented by the following illustrative equation:

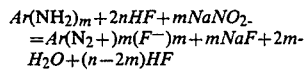

$$Ar(NH_2)_m + 2nHF + mNaNO_2$$
$$= Ar(N_2+)m(F^-)_m + mNaF + 2m\text{-}H_2O + (n-2m)HF$$

wherein n is greater than or equal to 2m.

Hydrogen fluoride acts as both a reactant (i.e., a source of fluorine for the aromatic diazonium fluoride being prepared) and as the medium for the diazotization reaction. In order to serve as the reaction medium, there is employed an amount of HF in excess of the amount of HF required for use as such reactant.

A preferred method of producing aromatic diazonium fluoride for decomposition in accordance with the process of this invention is described in copending application Ser. No. 07/124,500 filed Nov. 24, 1987 by N. J. Stepaniuk and B. J. Lamb, the disclosure of which is incorporated herein by reference.

In general, a diazotization agent such as sodium nitrite is added with agitating to a solution of the aromatic primary amine in excess anhydrous hydrogen fluoride. The resulting diazotization reaction mixture is maintained at a temperature which is sufficiently high to be effective for diazotization but not so high as to result in an unacceptable amount of decomposition of the resulting aromatic diazonium fluoride. Such temperature depends on which aromatic amine is being diazotized. In general, the temperature is from about $-5°$ C. to $50°$ C., preferably $-5°$ C. to $30°$ C. The sodium nitrite may be added as a solid, as described by Osswald et al. in German Pat. No. 600,706 for diazotization of aniline to benzene diazonium fluoride in excess anhydrous HF. Alternatively, sodium nitrite may be added as a solution prepared by dissolution thereof in anhydrous hydrogen fluoride (generating nitrous acid in HF) as described in above-cited Japanese Patent Publication No. 49[1974]-81330, published Aug. 6, 1974, for its one-step diazotization-fluorination.

Any aromatic amine which is diazotizable under HF conditions can be converted to the corresponding aromatic diazonium fluoride, which can then be decomposed to the corresponding aromatic fluoride using the process of this invention. Such diazotizable aromatic amines include diazotizable carbocyclic aromatic primary amines (e.g. aminobenzenes) and heterocyclic aromatic primary amines (e.g. amino pyridines), including heterocyclic aromatic primary amines containing structures wherein benzene is condensed with a heterocyclic ring. Included by such amines are carbocyclic and heterocyclic mono-amines and carbocyclic and heterocyclic polyamines (e.g. diamines). Such amines include, for example, amines derived from such carbocyclic aromatic compounds as benzene, biphenyl, diphenylmethane, diphenyl ether, condensed benzenoids such as naphthalene and anthracene, and from such heterocyclic aromatic compounds as pyridine, quinoline and isoquinoline. The aromatic ring or rings in the aromatic amines may be unsubstituted or substituted with one or more substituents selected from the group consisting of alkyl (e.g. linear or branched alkyl having 1 to 12, preferably 1 to 4, carbon atoms), alkoxy (e.g. linear or branched alkoxy having 1 to 12, preferably 1-4, carbon atoms), halo (e.g. chloro, fluoro and bromo), nitro, cyano, acyl (e.g. linear or branched acyl having 1-4 carbon atoms, such as acetyl), acylamino (e.g. acetylamino), carboxy, keto, aldo and hydroxy.

Suitable carbocyclic aromatic primary amines include, for example, aniline; methoxyaniline (e.g. para-anisidine); chloroaniline and bromoaniline in which the chloro or bromo group is in the ortho, meta or para position relative to the amine group; toluidines such as ortho-, meta- and para-aminotoluene, and ring-halogenated (e.g. ring-chlorinated or ring-brominated) derivatives of such toluidines, e.g. 2-chloro-6-aminotoluene (also called 6-chloro-ortho-toluidine); ortho-, meta- and para-phenylene diamine; methylene dianilines such as 3,3'- 4,4'- and 3,4'-methylene dianiline; biphenyl amines, e.g. 2-amino-biphenyl, 4-amino-biphenyl, 3,3'-diamino-biphenyl, 4,4'-diamino-biphenyl and 3,4'-diamine biphenyl; and ring-halogenated biphenyl amines, e.g. 3,3'-dichloro-4,4'-diamino-biphenyl (i.e. 3,3'-dichlorobenzidine, which rapidly undergoes diazotization). Suitable heterocyclic aromatic primary amines include, for example, 2-, 3- and 4-aminopyridine; diaminopyridines such as 2,6-diaminopyridie; haloaminopyrdine such as 2-amino-4,5- and 6-chloropyridine and 3-amino-5- and 6-chloropyridine; nitroaminopyridines such as 2-amino-5-nitropyridine; and alkylaminopyridines such as 2-amino-4-, 5- and 6-methyl-pyridine and 2-amino-4,6-dimethylpyridine.

In a preferred embodiment of the invention, the aromatic diazonium fluoride, which is produced from aniline, is benzene diazonium fluoride. Benzene diazonium fluoride is decomposed to produce fluorobenzene using the process of this invention.

In accordance with the preferred embodiment of the invention, a liquid feed solution of aromatic diazonium fluoride in hydrogen fluoride is continuously fed to at least the first of a plurality of sequential reaction vessels. The feed solution typically contains from about 0.5 gram-mole/liter to about 3.0 gram-moles/liter of diazonium fluoride. Preferably it contains from about 1.0 gram-mole/liter to about 3.0 gram-moles/liter. Most preferably, the feed contains about 2.5 gram-moles/liter. Any suitable stirred reaction vessels that are inert to the reactants and products can be employed. Suitable reaction vessels include round bottom tanks equipped with propeller agitators, cooling coils and jackets with appropriate piping, nozzles, etc.

While there is no actual limit to the number of sequential reaction vessels that can be employed, it is preferred to employ two sequential stirred-tank reactors, wherein partial decomposition of diazonium fluoride takes place in the first vessel. The effluent from the first vessel is continuously fed to the second vessel where decomposition is essentially completed. If desired, the continuous process of the invention can also be carried out using a single stirred-tank reactor.

If desired, the liquid feed solution of diazonium fluoride can be fed to two or more of the reaction vessels, provided only that the concentration of diazonium fluoridein each vessel is maintained at a level not greater than 2.0 gram-moles per liter preferably not greater than 0.5 gram-moles per liter. It is preferred, however, not to provide liquid feed solution to the last reaction vessel.

The reaction vessels are agitated in order to reduce local concentration zones of segregated diazonium fluoride feed. In order to achieve the desired degree of mixing, it is preferred that the feed inlet be located proximally to the mixing means, e.g. the agitator blades. Preferably, the feed inlet is configured to feed diazonium solution directly onto the agitator blades, such as, for example, by introducing the feed solution through a dip tube directly onto the agitator blades. Introduction of the concentrated diazonium into hot decomposer heel can also be accomplished by an external pump mixing loop wherein a portion of the first reactor contents is withdrawn by a pump, blended with the cold incoming diazonium, and mixed thorougly and rapidly by a static mixer type device before introduction into the same reactor. This permits the mixing load to be taken off the reactor and located in the mixing loop. It allow elimination of the agitator and use of the pump loop for all tank mixing needs. It also permits temperature adjustment of recycled heel by cooling in an in-line heat exchanger before the diazonium solution introduction point, thus permitting thorough mixing in a cold zone, an advantage in avoiding side reactions that occur with hot full strength diazonium solutions.

The reaction vessels are heated to maintain the reactors at a temperature insuring a high rate of decomposition. Decomposition of the diazonium fluoride can be carried out over a wide range of temperatures, with the rate of decomposition being temperature dependent. Typically, the decomposition is carried out at a temperature from about 30° C. to 80° C. Preferably, benzene diazonium fluorde is decomposed at a temperature from about 35° C. to 45° C., most preferably at about 40° C.

Partial conversion of the aromatic diazonium fluoride to aromatic fluoride takes place in the first reactor, typically about 90% conversion. The reaction mixture in the first reaction vessel is continuously withdrawn and fed to the second reaction vessel, where further decomposition occurs, and so on until substantially all of the diazonium fluoride has been converted to aromatic fluoride in the last reaction vessel. Using the process of the invention overall conversion of substantially all of the diazonium fluoride can be achieved, for example and 98 to 99.5% of the diazonium floride is converted. Approximately 90% of the conversion product is the desired aromatic fluoride. The aromatic fluoride can be separated from soluble by products by conventional techniques, such as distillation.

The rates of feed and withdrawal are maintained such that the concentration of diazonium fluoride in the reaction vessels is not greater than 2.0 gram-moles per liter, perferably not greater than 0.5 gram-moles per liter and the diazonium fluoride has been substantially completely converted to aromatic fluoride in the last reactor. The particular feed rate will depend on feed concentration, reactor size, number of reactors and rate of decomposition (which is dependent on the particular diazonium fluoride being converted and the decomposition temperature). Based on these factors, the skilled worker can calculate the feed rates. Typically, using two 1200-gal. reactors and a dcomposition temperature of 40° C. for benzene diazonium fluoride at a feed concentration of 2.5 gram-mole/liter, essentially complete conversion can be achieved at a flow rate of about 5 gal./min.

The invention can be further understood with reference to FIG. 1, which is a schematic flow diagram of a preferred embodiment of the invention. A solution of aromatic diazonium fluoride, e.g. benzene diazonium fluoride, is fed from holding tank 10 by means of a pump 12 through line 14 and dip tube 42 into a first continuous stirred tank reactor 16, where it is fed directly onto the agitator blades 46. Prior to commencing the flow of diazonium fluoride, the reactors 16 and 26 are charged with a "heel". The term "heel" refers to the remainder of the decomposed diazonium solution after the organic layer is separated. The heel qenerally comprises hydrogen fluoride, water and sodium fluoride with about 1% entrained organic compounds. If no heel is available from a previous composition, a synthetic heel is prepared, which typically contains 68% hydrogen fluoride, 11% water and 21% sodium fluoride by weight. The temperature of the heel is raised to about 35° C. to 45° C. prior to commencing the flow of aromatic diazonium fluoride. By using appropriate temperature control means (not shown) the temperature of the diazonium fluoride in reactor 16 is maintained at between 35° C. and 45° C.

The diazonium fluoride undergoes decomposition, releasing nitrogen gas. The reactor 16 is maintained at near atmospheric pressure but preferably between 0 and 35 psia and the nitrogen gas passes through line 20 and through two sequential condensers 22 and 24 where any HF vapor and aromatic fluoride product, e.g. fluorobenzene, is separated as a liquid. The liquid overflow from reactor 16 passes through line 18 into a second continuous stirred tank reactor 26. The effluent from reactor 16 preferably has undergone about 90% conversion of aromatic diazonium fluoride to aromatic fluoride.

The remainder of the aromatic diazonium fluoride is decomposed to aromatic fluoride in reactor 26. Nitrogen gas leaves reactor 26 via line 28 and passes through two sequential condensers 30 and 32 where HF vapor and aromatic fluoride product is separated as a liquid. Nitrogen from condensers 24 and 32 passes through line 34 and 36 to scrubber 38 where any trace amounts of aromatic fluoride and HF are removed. The product overflows from tank 26 and it is collected in a suitable receiving vessel 40. Typically, the product stream contains at least 99 mol. % aromatic fluoride, based on the aromatic diazonium fluoride in the feed.

The bottoms product (condensate) from condensers 22 and 24, containing HF and some aromatic fluoride product, is normally refluxed to reactor 16. Likewise, the bottoms product from condensers 30 and 32 is normally recycled to reactor 26. If desired, however, the reactors can be operated with forward distillation, wherein the condensate is not returned to the reactor but is sent forward to a receiving vessel. The preferred design is to return the condensate to maintain the HF concentration in the liquid phase at a maximum for yield optimums. This then necessitates operation slightly above atmospheric pressure. This pressure will vary from product to product, and is generally 0 to 50 psig, most normally 2 to 20 psig. The system pressure can be further regulated by a back pressure device to maintain a nitrogen blanket on the reactors, which will have design benefits in reducing the condensible vapor loads being swept through the condensing system by by product nitrogen. An alternate design, allowing condensate to flow forward, permits atmospheric pressure operation of the decomposers. In this design, the reactor contents reach an equilibrium with atmospheric pressure by flashing off the volatiles until they produced a vapor pressure about that of atmospheric pressure. This permits atmospheric pressure operation but in a more concentrated system, having slightly less HF in the reaction solution. This is expected to slightly lower the product yield because of higher by product formation, and will require a slightly larger condensing system than that pressurized total reflux design.

Practice of this invention is further illustrated by the following non-limiting examples. All parts, percents and other amounts throughout this disclosure are by weight unless otherwise indicated.

EXAMPLE 1

There was prepared 9 liters (11.43 kg) of a diazonium fluoride solution including 21.6 gram-moles (g-moles) of benzene diazonium fluoride in hydrogen fluoride (HF). The concentration of diazonium fluoride in the solution was 2.40 g-moles/liter.

First and second vessels substantially as illustrated by vessels 16 and 26, each of 1.6-gallon capacity, were filled to the point of overflow with a "synthetic heel" solution of hydrogen fluoride (HF), sodium fluoride (NaF) and water. The synthetic heel was prepared in each vessel by adding thereto with stirring hydrogen fluoride (5,406 grams, 270 g-moles), water (874.5 grams, 48.6 g-moles) and NaF (1669 grams, 39.7 g-moles) while maintaining the temperature of the solution at 0° C. The solution in each vessel was then heated to 40° C. by circulating 40° C. water in the reactor jackets.

The diazonium fluoride solution was then continuously supplied at a temperature of 0° C. and a flow rate of 25 ml/min, 0.06 g-mole/min of the diazonium fluoride, to the heel solution in the first vessel with continuous stirring. The temperature of the solution in the first vessel was maintained at 40° C. throughout the 6-hour run. The diazonium fluoride solution was introduced below the surface of the liquid in the first vessel and adjacent the impeller of the agitator employed for stirring.

The stirring reaction mixture in the first reactor vessel continuously overflowed at approximately 25 ml/min. via the overflow line into the second reactor vessel. The reaction mixture in the second vessel is also continuously agitated and maintained at about 40° C. The overflow line entering the second reactor vessel was at the surface of liquid reaction mixture therein. The concentration of diazonium in this stage is sufficiently low not to necessitate special provisions for efficient local mixing of entry feed.

Analysis of samples taken at intervals of 60 minutes of the overflow stream exiting the first reactor showed the presence therein of benzene diazonium fluoride in concentrations of from about 0.216 to about 0.264 g-moles per liter. This corresponds to conversion of approximately 90% of the benzene diazonium fluoride to fluorobenzene in the first reaction vessel. Calculation shows that residual diazonium fluoride was entering the second reaction vessel (in the entering overflow) at about 0.006 g-mole/minute.

The stirring reaction mixture in the second reactor vessel continuously overflowed through its product overflow line at about 25 ml/minute. Analysis of samples taken at intervals of 60 minutes of the product overflow stream exiting the second reactor showed the presence therein of benzene diazonium fluoride in an amount corresponding to about 99% conversion, based on the amount of benzene diazonium fluoride introduced into the reaction system.

Condensers 22, 24, 30, and 32 condensed fluorobenzene and HF vapors evolved from the reaction mixtures in the corresponding reactor vessels during the decomposition run. The condensate was returned to the vessels by gravity in the manner of reflux. The condensers were vented to scrubber 38 where the evolved non-condensed gases were scrubbed with 20% NaOH in water, thereby increasing recovery of fluorobenzene which otherwise would have been lost.

After the 6-hour run was completed, the solutions in vessels 16 and 26 were cooled to 20° C., via cooling water, and added to the solution in product receiver 40. The product solution was then decanted, and the upper crude fluorobenzene layer and the lower acid layer were analyzed with the following results:

| Name | | g-Mole | % of 21.6 g-moles Diazonium Fluoride |
|---|---|---|---|
| Fluorobenzene | | 19.44 | 90% |
| Phenol | | 0.43 | 2% |
| 2 and 4-Hydroxybiphenyl | (a) | 0.22 | 1% |
| 2 and 4-Fluorobiphenyl | (b) | 0.30 | 1.4% |
| Other organics | | 1.21 | 5.6% |

What is claimed is:

1. A process for continuous preparation of an aromatic carbocyclic or heterocyclic fluoride from the corresponding aromatic diazonim fluoride which comprises:
    (a) continuously introducing to at least the first of one or more sequential reaction vessels a liquid feed solution of an aromatic diazonium fluoride in hydrogen fluoride;
    (b) continuously agitating the reaction mixtures in the reaction vessels while heating the contents of the vessels to a remperature sufficient to decompose said diazonium fluoride; and
    (c) continuously withdrawing reaction mixture from each of said reaction vessels and feeding withdrawn reaction mixture to next successive reaction vessel until the decomposition of said diazonium fluoride is substantially complete, the withdrawal and feed rates being sufficient to maintain the concentration of diazonium fluoride in the reacrion mixtures in each of the vessels at not more than 2.0 gram moles per liter.

2. The process of claim 1, wherein the aromatic diazonium fluoride is fed to the reaction vessel by withdrawing a portion of the reactor contents, mixing the withdrawn reactor contents witn the aromatic diazonium fluoride feed in a static mixer and introducing the mixture into the reactor.

3. The process of claim 2, wherein the concentration of aromatic diazonium fluoride in the mixture is less than 2.0 gram-moles per liter.

4. The process of claim 1, wherein the concentration of aromatic diazonium fluoride in each of the reaction vessels is not greater than 0.5 gram-moles per liter.

5. The process of claim 2, wherein the concentration of aromatic diazonium fluoride in the mixture is less than 0.5 gram-moles per liter.

6. The process of claim 1, wherein there are two sequential reaction vessels.

7. The process of claim 1, wherein the aromatic fluoride is fluorobenzene and the aromatic diazonium fluoride is benzene diazonium fluoride.

8. The process of claim 1, wherein the liquid feed solution contains from about 0.5 gram-moles per liter to about 3.0 gram-moles per liter of aromatic diazonium fluoride.

9. The process of claim 1, wherein the liquid feed solution contains from about 1.0 gram-mole per liter to about 3.0 gram-moles per liter of aromatic diazonium fluoride.

10. The process of claim 1, wherein the vessels are stirred with agitator blades and the feed mixture is fed to the first reaction vessel at a point that is proximal to said blades.

11. The process of claim 7, wherein the decomposition temperature is from about 35° C. to about 45° C.

12. The process of claim 6, wherein at least 90% of the aromatic diazonium fluoride is converted to aromatic fluoride in the first reactor.

* * * * *

UNITED STATES PATENT AND TRADEMARK OFFICE
CERTIFICATE OF CORRECTION

PATENT NO. : 4,822,927

DATED : April 18, 1989

INVENTOR(S) : Stepaniuk et al.

It is certified that error appears in the above-identified patent and that said Letters Patent is hereby corrected as shown below:

Col. 2, line 6, "by products" should be --by-products--.

Col. 2, line 52 "perferable" should be --preferably--.

Col. 2, lines 65-66, "by products" should be --by-products--.

Col. 2, line 66, "By products" should be --By-products--.

Col. 5, line 6, "fluoridein" should be --fluoride in--

Col. 5, line 28, "allow" should be --allows--.

Col. 5, line 42, "florde" should be --fluoride--.

Col. 6, line 3, "dcomposition" should be --decomposition--.

Col. 6, line 53, "fluoride" should be --products--.

Col. 8, line 46, "remperature" should be --temperature--.

Signed and Sealed this

Twentieth Day of March, 1990

Attest:

JEFFREY M. SAMUELS

Attesting Officer

Acting Commissioner of Patents and Trademarks